(12) United States Patent
Levine

(10) Patent No.: US 8,086,308 B2
(45) Date of Patent: *Dec. 27, 2011

(54) IMPLANTABLE MEDICAL DEVICE FOR IDENTIFYING AND MANAGING INTRINSIC REENTRANT TACHYCARDIA

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 811 days.

This patent is subject to a terminal disclaimer.

(21) Appl. No.: 12/144,351

(22) Filed: Jun. 23, 2008

(65) Prior Publication Data

US 2009/0005828 A1 Jan. 1, 2009

Related U.S. Application Data

(63) Continuation-in-part of application No. 11/769,602, filed on Jun. 27, 2007, now Pat. No. 7,986,993.

(51) Int. Cl.
*A61N 1/18* (2006.01)
(52) U.S. Cl. .................... 607/9; 607/17; 607/25
(58) Field of Classification Search ............... 607/9, 30, 607/17
See application file for complete search history.

(56) References Cited

U.S. PATENT DOCUMENTS

| | | | |
|---|---|---|---|
| 4,788,980 A | 12/1988 | Mann et al. | |
| 5,674,257 A | 10/1997 | Stroebel | |
| 6,243,606 B1 | 6/2001 | Mann et al. | |
| 6,259,950 B1 | 7/2001 | Mann et al. | |
| 6,263,244 B1 | 7/2001 | Mann et al. | |
| 6,285,908 B1 | 9/2001 | Mann et al. | |
| 6,498,949 B2 | 12/2002 | Levine et al. | |
| 6,584,354 B1 | 6/2003 | Mann et al. | |
| 6,618,622 B1 | 9/2003 | Mann et al. | |
| 6,792,307 B1 * | 9/2004 | Levine et al. | 607/9 |
| 6,862,477 B1 | 3/2005 | Mo | |
| 7,146,215 B1 | 12/2006 | Mo | |
| 7,636,598 B2 * | 12/2009 | Husby | 607/9 |
| 2008/0091244 A1 * | 4/2008 | Richardson | 607/9 |
| 2008/0140147 A1 * | 6/2008 | Husby | 607/30 |

FOREIGN PATENT DOCUMENTS

| | | |
|---|---|---|
| EP | 0308535 B1 | 3/1993 |
| WO | 2006065707 A2 | 6/2006 |

OTHER PUBLICATIONS

Levine, Paul A. MD, "Postventricular Atrial Refractory Periods and Pacemaker Mediated Tachycardias," Clin. Prog. in Pacing and Electrophysiol. 1983:1(4):394-401.

(Continued)

*Primary Examiner* — Carl H. Layno
*Assistant Examiner* — Jon-Eric C. Morales

(57) ABSTRACT

An implantable medical device is provided that comprises a pulse generator that provides atrial and ventricular pacing pulses on demand. The pulse generator times delivery of the ventricular pacing pulses based on an AV pacing interval. The device also includes an AV hysteresis module that extends the AV interval from a base AV interval to an extended AV interval to promote intrinsic heart activity. A refractory module establishes a PVARP interval equal to base PVARP interval following at least one of the ventricular pacing pulses. The refractory module lengthens the PVARP interval by adding a PVARP extension to a base PVARP interval to provide an extended PVARP interval. The device further includes a reentrant conduction detector that identifies an intrinsic reentrant tachycardia having a retrograde P wave occurring during the PVARP extension, based on one or more of i) a retrograde P wave, ii) intrinsic R waves sensed over N cardiac cycles at an R to R interval above a rate threshold and iii) one or more of PR and RP intervals that exceed PR and RP thresholds.

21 Claims, 8 Drawing Sheets

OTHER PUBLICATIONS

Dennis, Malcolm J. et al., "Pacemaker Mediated Tachycardia as a Complication of the Autointrinsic Conduction Search Function," PACE. 2004;27(Pt I):824-826.

Levine, Paul A., "Letters to the Editor," PACE. 2004;27:1691-1693.

Olshansky, Brian MD et al., "Pacemaker-Mediated Tachycardia," www.emedicine.com, Aug. 9, 2006.

* cited by examiner

IMPLANTABLE MEDICAL DEVICE FOR IDENTIFYING AND MANAGING INTRINSIC REENTRANT TACHYCARDIA

This application is a continuation-in-part of U.S. patent application Ser. No. 11/769,602, filed Jun. 27, 2007, titled "Implantable Cardiac Device Providing AV Interval Hysteresis to Promote Intrinsic Conduction While Providing PMT Avoidance and Method", now U.S. Pat. No. 7,986,993.

FIELD OF THE INVENTION

The present invention generally relates to the field of implantable medical devices. Embodiments of the present invention more particularly relate to implantable medical devices that identify and manage intrinsic reentrant tachycardia that may occur during AV hysteresis evaluation.

BACKGROUND OF THE INVENTION

Implantable cardiac devices are well known in the art. They may take the form of implantable defibrillators or cardioverters which treat accelerated rhythms of the heart such as fibrillation. They may also take the form of implantable pacemakers which maintain the heart rate above a prescribed limit, such as, for example, to treat a bradycardia. Implantable cardiac devices are also known which incorporate both a pacemaker and a defibrillator.

A pacemaker is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Further, pacing systems are known which pace at multiple sites. For example, biventricular pacing paces in both ventricles and biatrial pacing paces in both atria. Hence, it is possible, that a heart may be paced in all four chambers.

A popular mode of operation for dual-chamber pacemakers is the DDD mode. Specifically, DDD systems provide atrial pacing during atrial bradycardia, ventricle pacing during ventricular bradycardia, and atrial and ventricular pacing during combined atrial and ventricular bradycardia or heart block also known as AV block. In addition, DDDR systems monitor patient activity levels for controlling pacing rate to more closely approximate the normal response of the heart to exercise, or other physiological activity demanding a faster heart rate.

Recently, pacing therapies have been advanced which encourage intrinsic ventricular activity. One such system employs an auto intrinsic conduction search (AICS) wherein the pacemaker utilizes two AV intervals. The first AV interval is a programmable base AV interval to support ventricular demand pacing. The second AV interval is an extended AV interval which may be thought of as comprising the base AV interval with an AV interval extension added to its end. An AICS is one example of an AV hysteresis algorithm. Other AV hysteresis algorithms to promote or encourage intrinsic conduction through AV interval extension have been advanced. Some AV hysteresis algorithms extend the AV interval on a periodic basis in order to search for sensed (intrinsic) R waves. The term AV hysteresis, as used throughout, shall mean any method involving AV interval extension to encourage intrinsic ventricular activity. It has been proposed to extend the PVARP interval to a duration longer than a normal (base) PVARP interval when the AV hysteresis algorithm lengthens the AV interval from the base AV interval to an extended AV interval. The term AV interval, as used throughout, shall be used to refer to an interval between a paced (A) pulse in the atrium, or a sensed P wave, and a paced (V) pulse in the ventricle.

During the extended AV interval, the atrium may have recovered on a physiologic basis to allow retrograde conduction to occur following the ventricular paced (V) or sensed (R) event and the initiation of a pacemaker mediated tachycardia (PMT). Repeated stimulation at a high rate can thereafter be sustained by heart tissue retrograde conduction combined with functional anterograde conduction that is modeled by the pacemaker when sensing the intrinsic, in this case retrograde, atrial depolarization and triggering a ventricular stimulus to be delivered at the end of the programmed AV delay. One method for preventing PMTs involves the use of programmable post-ventricular atrial refractory periods (PVARP), where the PVARP is programmed to be longer than the retrograde conduction interval.

In addition to potential PMT's, other arrhythmic heart rhythms may occur while an AV hysteresis algorithm is searching for intrinsic conduction, such as a repetitive non-reentrant ventriculo-atrial synchronous (RNRVAS) rhythm. The RNRVAS rhythm is fully described, for example, in U.S. Pat. No. 6,498,949 B2,which patent is incorporated herein in its entirety.

Examples of arrhythmic heart rhythms, that may occur when an AV hysteresis algorithm is activated, include i) AV reentrant tachycardia (AVRT) including anterograde reentrant tachycardia via the AV nodal tissue also called an orthodromic AVRT, ii) retrograde reentrant tachycardia via the AV nodal tissue called antidromic AVRT and iii) AV nodal reentrant tachycardia (AVNRT), which shall collectively be referred to hereafter as supraventricular reentrant tachycardia. Antidromic conduction is the progression of electrical activity from the atria to the ventricles through an accessory pathway with conduction back to the atrium in a backward direction from the ventricle to the atria via the AV node. Orthodromic reentrant tachycardia occurs when the electrical activity progresses from the atria to the ventricle through the AV node and returns to the atrium from the ventricle via the accessory pathway. This circular progression continues and overrides the normal conduction system. It is possible, during the extension of the AV delay in association with the AV hysteresis algorithm that retrograde conduction is allowed to occur placing an intrinsic, but retrograde, P wave that temporally coincides with an extended PVARP and is not tracked. The P wave conducts anterograde from the atrium to the ventricle with a long PR interval via either an path of slow conduction within the AV node or an accessory pathway and may then return to the atria in a retrograde manner through a second pathway, again within either the AV node or an accessory pathway, thereby allowing for sustained intrinsic supraventricular reentrant tachycardia.

Periodic extensions of the AV interval and PVARP interval may inadvertently permit retrograde conduction at the longer AV intervals in individuals who have either an accessory pathway or dual-AV nodal pathways. This is analogous to an atrial premature beat reaching the AV node when the AV node is not yet fully recovered. It occurs early in the cardiac cycle when only one of the two pathways is recovered, which may represent the pathway with slow forward conduction as it tends to have a relatively rapid recovery period. The atrial premature beat is conducted but only down the slow pathway. While the premature beat conducts down the slow pathway, the fast pathway has additional time to recover. When the forward or anterograde conduction reaches the bottom of the slow pathway within the AV node, it now finds the fast pathway fully recovered allowing it to echo back through the fast pathway. In the patient who can sustain this combination, the atrial premature beat initiates a reentrant tachycardia, in the case described within the tissue of, or surrounding, the AV node. As long as there are at least two pathways in the heart between the atrium and the ventricle with intacted antero-grade conduction through the AV node via one pathway when the AV delay is extended, the impulse can echo backwards through the second pathway. The extended PVARP may place the retrograde P wave in the PVARP interval. Hence, the retrograde P wave may not be tracked (e.g. to avoid a PMT), yet based on the patient's intrinsic electrophysiology, there may still be an intrinsic supraventricular tachycardia in association with intrinsic electrophysiologic properties of the patient's heart.

A need remains for an implantable medical device that identifies and manages intrinsic reentrant tachycardia that may be initiated by the normal AV hysteresis behavior because this unmasks electrophysiologic properties of the heart that had not been previously appreciated.

SUMMARY OF THE INVENTION

In accordance with one embodiment, an implantable medical device is provided that comprises a pulse generator that provides atrial and ventricular pacing pulses on demand. The pulse generator times delivery of the ventricular pacing pulses based on an AV pacing interval. The device also includes an AV hysteresis module that extends the AV interval from a base AV interval to an extended AV interval to promote intrinsic heart activity. A refractory module establishes a PVARP interval equal to a base PVARP interval following at least one of the ventricular pacing pulses. The refractory module lengthens the PVARP interval by adding a PVARP extension to a base PVARP interval to provide an extended PVARP interval. The device further includes a reentrant conduction detector that identifies an intrinsic reentrant tachycardia based on a retrograde P wave occurring during the PVARP extension of the extended PVARP interval.

In accordance with at least one embodiment, the reentrant conduction detector identifies the intrinsic reentrant tachycardia in part based on intrinsic R waves sensed over N consecutive cardiac cycles at a rate above a rate threshold. Optionally, the reentrant tachycardia may be based on an intrinsic QRS complex having PR and RP intervals that exceed corresponding PR and RP thresholds.

In accordance with one embodiment, the device further comprises a therapy control module that directs the pulse generator to provide a corrective therapy responsive to the reentrant conduction detector identifying the intrinsic reentrant tachycardia. Optionally, the therapy control module may deliver at least one ventricular pulse as the corrective therapy timed to follow the retrograde P wave by a delay less than the AV pacing interval. Optionally, the ventricular pulse may be delivered during the extended AV interval. The therapy control module may cause the pulse generator to repeat the corrective therapy during at least two successive cardiac cycles. The therapy control module may cause the pulse generator to repeat the corrective therapy on a programmable number of N consecutive cardiac cycles. In accordance with one embodiment, the AV hysteresis module restores the AV interval to the base AV interval and the refractory module restores the PVARP interval to a base PVARP responsive to delivery of a corrective therapy. Delivering the ventricular output pulse at a foreshortened paced or sensed AV delay may result in the interval between the R wave and subsequent ventricular paced event to be faster than the programmed maximum tracking interval for these cycles.

In accordance with one embodiment, a method is provided for managing a reentrant supraventricular tachyarrhythmia. The method comprises providing atrial and ventricular pacing stimulation pulses on demand. The ventricular pacing pulses is delivered based on a base AV interval. The method includes extending an AV interval from a base AV interval to an extended AV interval, and establishing a PVARP interval equal to a base PVARP interval following at least one of the ventricular pacing pulses. The PVARP interval is lengthened by adding a PVARP extension to the base PVARP interval. The method also includes identifying an intrinsic reentrant tachycardia occurring based on a retrograde P wave coinciding with the PVARP extension to then deliver a properly timed ventricular output at a shortened paced or sensed AV delay in an attempt to terminate the supraventricular reentrant tachycardia.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
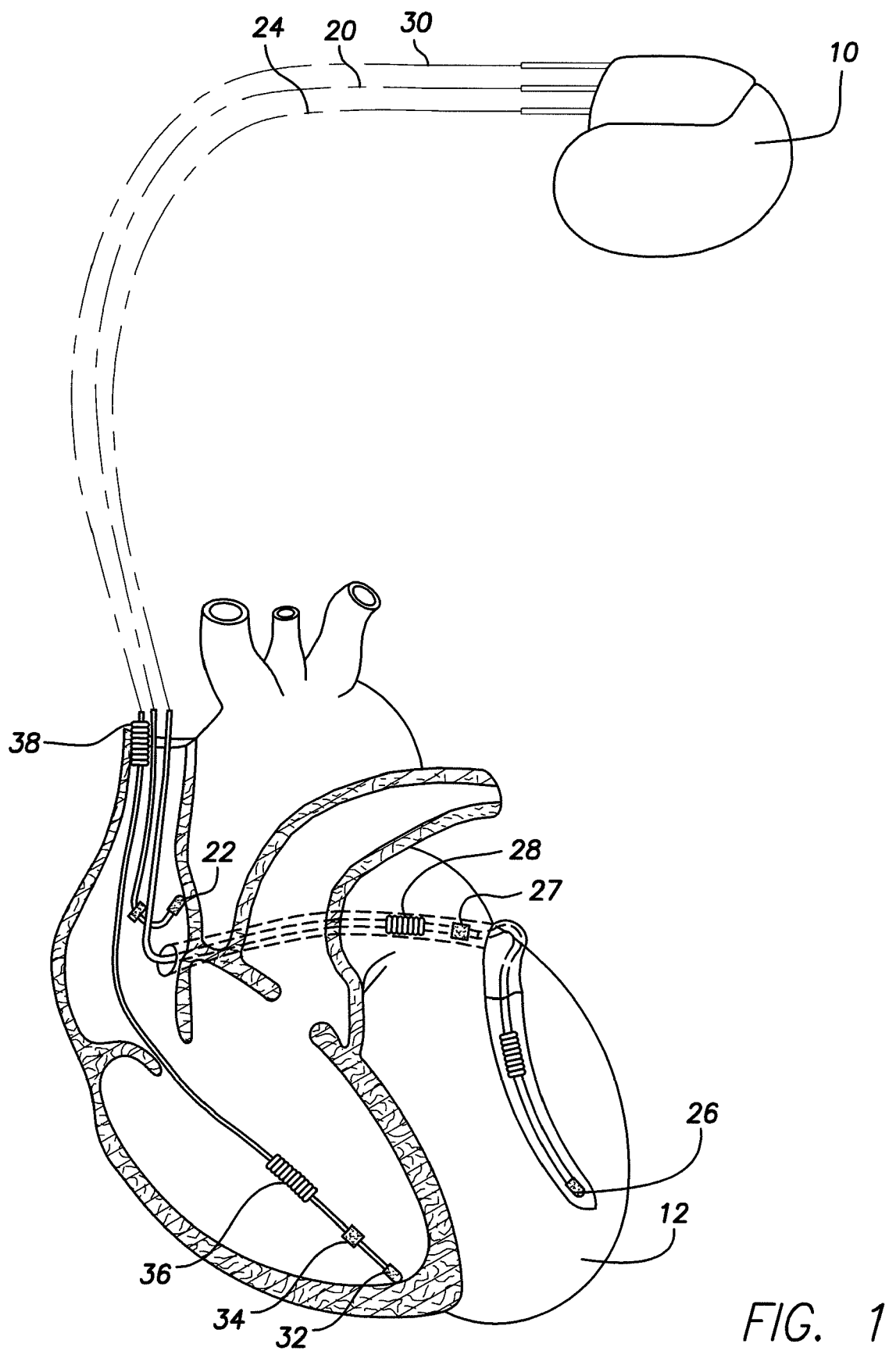
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrium.

To sense left atrial and ventricular cardiac signals and to provide left chamber pacing therapy, the medical or stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive left atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricle so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As explained below in more detail, the stimulation device 10 utilizes an AV hysteresis algorithm to search for intrinsic heart activity. The device 10 utilizes an arrhythmia detection process to recognize intrinsic reentrant tachycardia. In accordance with at least one embodiment, the arrhythmia detection module identifies the intrinsic reentrant tachycardia based on a retrograde P wave during the extended PVARP interval and based on intrinsic R waves sensed over N cardiac cycles at a rate above a rate threshold. In accordance with one embodiment, the device 10 further comprises a therapy control module that directs the pulse generator to provide a corrective therapy responsive to the arrhythmia detection module identifying the intrinsic reentrant tachycardia. Optionally, the therapy control module may deliver at least one ventricular pulse, as the corrective therapy, timed to follow the retrograde P wave by a delay less than the AV pacing interval. Optionally, the ventricular pulse may be delivered during the extended AV interval. The therapy control module may cause the pulse generator to repeat the corrective therapy during at least two successive cardiac cycles. The therapy control module may cause the pulse generator to repeat the corrective therapy during up to a programmable number of N successive cardiac cycles.

Figure 2:
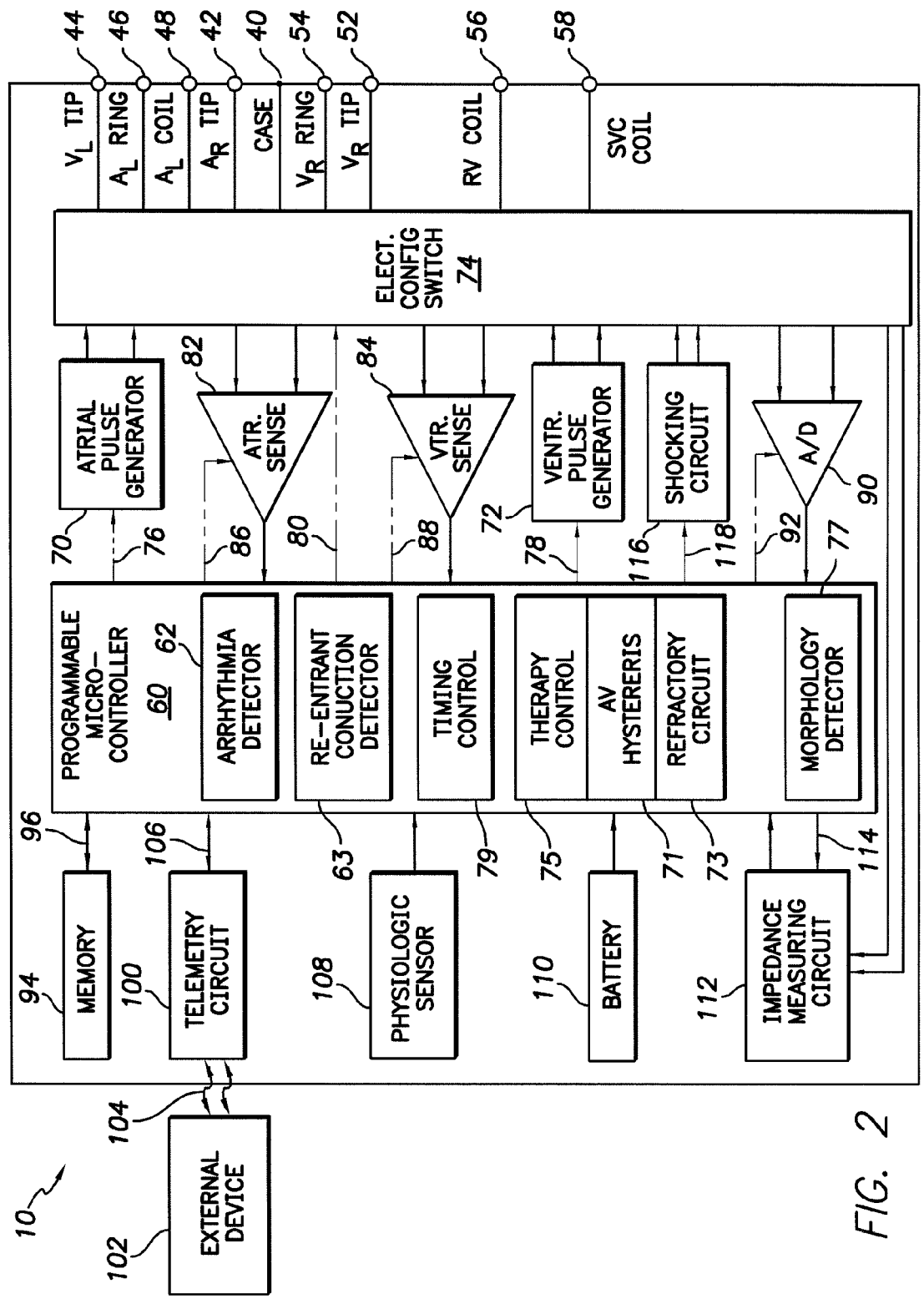
FIG. 2 is a functional block diagram of the implantable stimulation device of FIG. 1 illustrating an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The blocks illustrated in FIG. 2 represent functional blocks which may be implemented in hardware, discrete logic, firmware, software, in or with a single CPU, multiple CPUs, field programmable gate arrays and the like. The terms "circuit" and "module" are used throughout interchangeably to refer to functional blocks.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller or processor 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) interval or delay, ventricular-atrio (VA) interval or delay, atrial interconduction (A-A) delay, or ventricular interconduction (V-V) delay, etc.) as well as to keep track of the timing of blanking intervals, noise detection windows, evoked response windows, alert intervals, marker channel timing, etc., which is well known in the art. The microcontroller 60 also includes a refractory circuit 73. The refractory circuit 73 times refractory periods, including post ventricular atrial refractory periods (PVARP) as described subsequently.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

An arrhythmia detector 62 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed sequential signals and noting the presence of an arrhythmia.

The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

A reentrant conduction detector 63 seeks to identify intrinsic reentrant tachycardia involving the atria that might otherwise continue undeclared due, in part, to the occurrence of retrograde P waves during an extended PVARP interval. The reentrant conduction detector 63 identifies an intrinsic reentrant tachycardia based on several parameters, such as intrinsic P waves occurring during the extended AV interval, the PR interval, the RP interval and the R to R interval. For example, the reentrant conduction detector 63 may analyze a series of intrinsic R waves over N cardiac cycles and determine whether the R to R interval corresponds to a heart rate above a rate threshold. The rate threshold may be programmable and/or may be automatically adjusted by the device 10. When the reentrant conduction detector 63 identifies a retrograde P wave, it also searches for an intrinsic QRS complex with stable (e.g., repeating) RP and PR intervals that are indicative of reentrant tachycardia.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes. Optionally, other leads with multiple electrodes may be added to the system, to further improve the diagnosis and characterization of the tachyarrhythmia.

Advantageously, the data acquisition system 90 may be coupled to the microcontroller, or other detection circuitry for detecting an evoked response from the heart 12 in response to an applied stimulus, thereby aiding in the detection of "capture". Capture occurs when an electrical stimulus applied to the heart is of sufficient energy to depolarize the cardiac tissue. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection preferably occurs on a beat-by-beat basis associated with the autocapture algorithm. Preferably, the capture threshold search is performed as previously described.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, AV interval, AV extension, PVARP interval, PVARP extension, PR threshold, RP threshold, R to R threshold, rate threshold, electrode polarity, rate, sensitivity, automatic features, arrhythmia detection criteria, and the amplitude, waveshape and vector of each shocking pulse to be delivered to the patient's heart 12 within each respective therapy. The memory 94 may also store the number of corrective therapies to be delivered in successive cardiac cycles to attempt to correct an intrinsic reentrant tachycardia.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ a power source comprised or one or more lithium salts, for example lithium/silver vanadium pentoxide, or other battery technologies known in the art.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 5 joules), moderate (6 to 15 joules), or high energy (16 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level and/or synchronized with an R-wave and/or pertaining to the treatment of tachycardia. Defibrillation shocks are generally of moderate to high energy level, i.e., corresponding to outputs in the range of 16-40 joules. Although external ICDs deliver the shock asynchronously (since R-waves may be too disorganized and small) in the setting of ventricular fibrillation, the implantable devices still synchronize with a ventricular depolarization signal as fibrillatory signals as recorded from inside the heart may be very discrete.

Accordingly, the microcontroller 60 is capable of controlling the delivery of the shocking pulses of various energy levels depending on the detected rate and identification of the rhythm by the implanted ICD.

As may be noted, the device 10 further includes an AV hysteresis circuit 71 and a refractory circuit 73. The AV hysteresis circuit 71 initiates an AV interval extension to encourage intrinsic activity of the heart during demand pacing. The AV hysteresis circuit may be of the type as previously described that extends the AV interval from a base AV interval to an extended AV interval by adding to the base AV interval an AV interval extension. The AV interval extension may be a fixed programmable interval. The AV interval is extended after the time-out of a predetermined time period following the restoration of the AV interval from a previous AV interval extension. The AV interval extension remains until the delivery of a first ventricular pacing pulse is required. When the pacing pulse is issued, the AV interval is restored back to the base AV interval. The AV interval may be restored to the base AV interval in various circumstances as discussed throughout.

When the AV interval is extended by the AV hysteresis circuit 71, the refractory circuit 73 in turn extends the PVARP from a base value to an extended PVARP by adding a PVARP extension to the base PVARP. The PVARP extended may also be a fixed programmable interval. The extended PVARP is maintained until the AV interval is restored to the base AV interval value. During the PVARP, atrial activity is preferably still sensed but not responded to for initiating a new AV interval. When a retrograde P wave is sensed by sense amplifier 82 during an extended PVARP, the reentrant conduction detector 63 determines whether an intrinsic R wave occurs thereafter as explained below. The P wave sensed during the refractory period will be identified as $P_{SR}$ in this patent.

The device further includes a therapy control 75 that may be employed to initiate therapy for arrhythmic rhythms. The arrhythmic rhythm may be, for example, AVRT or an AVNRT rhythm, and the like. For example, the corrective therapy applied may include shortening the PV delay interval for at least one cardiac cycle to break the rhythm. When a series of retrograde P waves are each followed by intrinsic R waves, the reentrant conduction detector 63 analyzes one or more of the $P_{SR}R$ interval, $RP_{SR}$ interval and R to R interval between successive cycles. Based on the foregoing parameters, the reentrant conduction detector 63 may declare an intrinsic reentrant tachycardia in accordance with the processes of FIGS. 5-7. The retrograde P wave is used to trigger a ventricular pulse at a shorter $P_{SR}V$ delay to preclude further reentry. The $P_{SR}V$ delay is shortened to a duration less than the base AV interval and/or less than the AV pacing interval. By way of example, the $P_{SR}V$ delay may result in the AV interval being shortened to less than the maximum tracking interval for these cycles.

Figure 3:
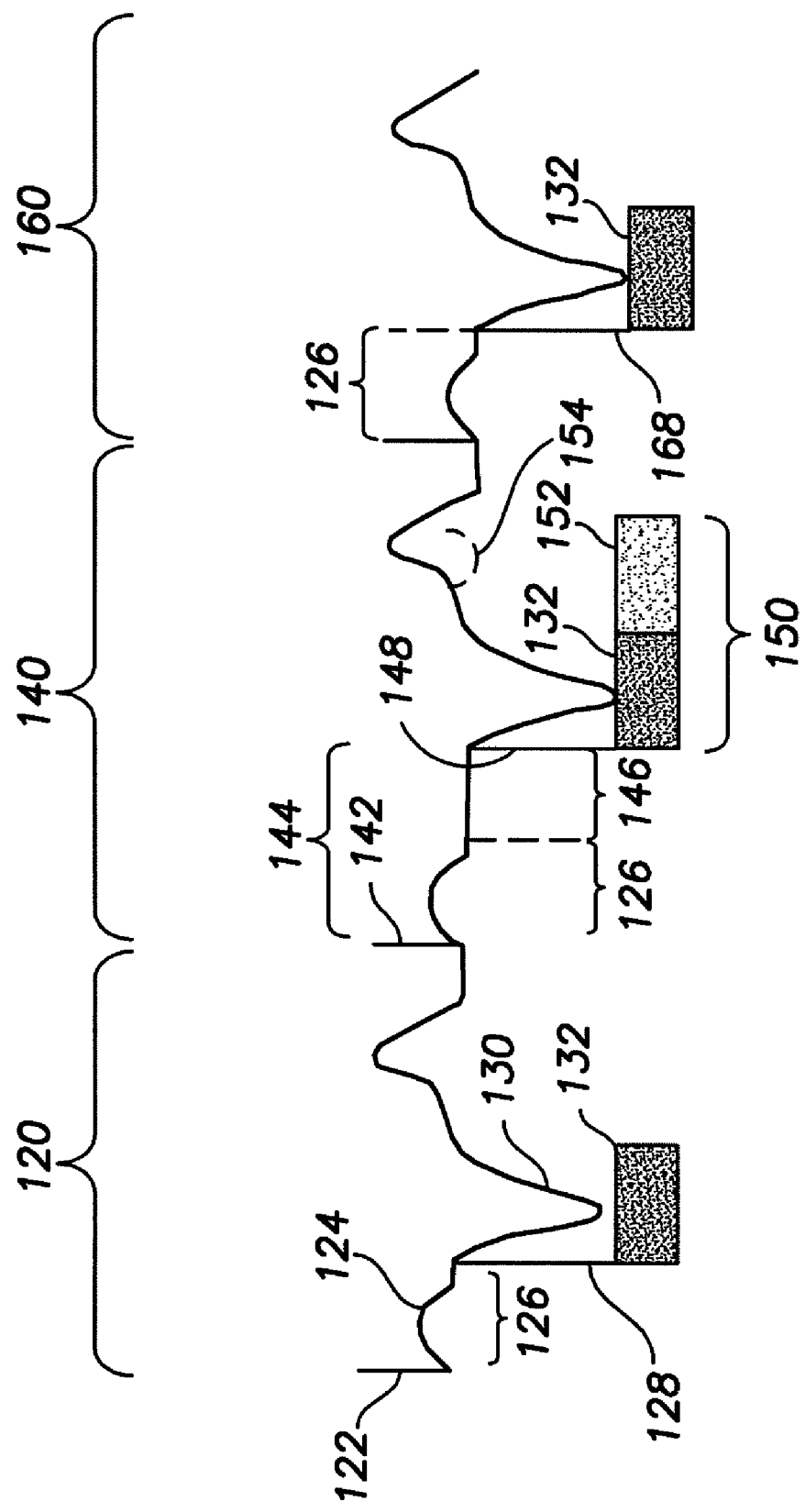
FIG. 3 is a timing diagram illustrating an embodiment of the present invention.

In FIG. 3, a timing diagram is shown describing the operation of the device 10 in connection with AV hysteresis evaluation. The timing diagram of FIG. 3 extends over three cardiac cycles 120, 140, and 160. In cardiac cycle 120, an atrial pacing pulse 122 causes an atrial evoked response 124. Then, after a base AV interval 126, a ventricular pacing pulse 128 is issued causing a ventricular evoked response 130. Upon issuance of the ventricular pacing pulse 128, the refractory circuit 73 (FIG. 2) provides a base PVARP 132.

During the cardiac cycle, a timer, such as timing control 79, times out to call for an AV interval extension by hysteresis circuit 71 to encourage intrinsic activity of the heart. Hence, upon the issuance of atrial pacing pulse 142, the AV hysteresis circuit 71 establishes an extended AV interval 144 comprising the base AV interval 126 and an added AV interval extension 146. Also, responsive to the AV interval extension 146 being established by the AV hysteresis circuit 71, the refractory circuit 73 establishes an extended PVARP 150 following the ventricular pacing pulse 148. The extended PVARP 150 comprises the base refractory period 132 plus a PVARP extension 152.

As may be noted in FIG. 3, the AV interval extension 146 has allowed a retrograde P wave 154. The retrograde P wave 154 might have caused a PMT to develop if it were not for the extended PVARP 150. More specifically, the retrograde P wave 154 has occurred during the extended PVARP 150. Hence, while the retrograde P wave 154 is sensed by the sensing circuit 82, it is not responded to for the initiation of an AV interval. Rather, a ventricular pacing pulse 168 is not again issued until it is regularly scheduled to issue.

Because the retrograde P wave 154 is sensed during the extended PVARP, the AV hysteresis circuit 71 responds by restoring the AV interval to the base AV interval 126 in the next cardiac cycle 160. The refractory circuit 73 then responds to the AV hysteresis circuit 71 restoring the AV interval to the base AV interval 126 and also restores the PVARP to the base PVARP 132 during the next cardiac cycle 160.

If there is a $P_{SR}$ wave sensed during the extended PVARP 150, cardiac cycle 140 may be repeated for a programmable number of cycles, default being 1, to assure that the P wave 154 detected within the PVARP extension 152 is consistent and related to the ventricular paced pulse 148 associated with the extended AV interval 144 rather than a coincidental native P wave. If P wave 154 was coincidental, it would not be present in the subsequent cardiac cycles.

Figure 4:
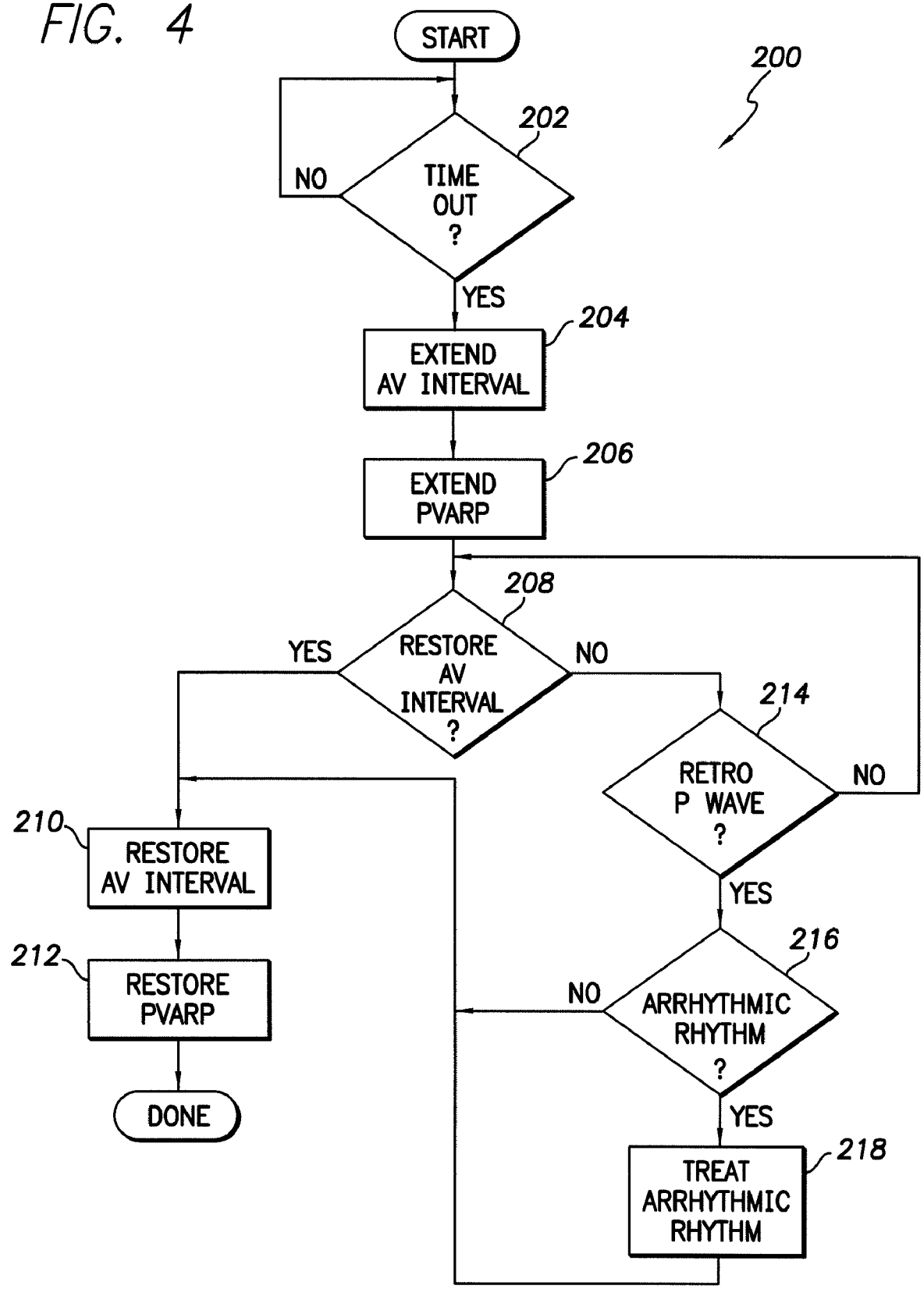
FIG. 4 is a flow chart describing an overview of the operation of one embodiment of the present invention.

FIG. 4 illustrates a flow chart describing an overview of the operation as implemented in one embodiment of the device 10 operating in a mode wherein AV pacing with AV hysteresis is enabled. In this flow chart the various algorithmic steps are summarized in individual "blocks". Such blocks describe specific actions or decisions made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process 200 of FIG. 4 initiates with decision block 202. Here it is determined if it is time for the hysteresis circuit 71 to extend the AV interval to encourage intrinsic activity of the heart. If not, the process returns. If it is time to extend the AV interval, the process advances to activity block 204 where the hysteresis circuit 71 extends the AV interval by, for example, adding an AV interval extension to a base AV interval. The process then advances to activity block 206 where, responsive to the hysteresis circuit 71 extending the AV interval, the refractory circuit 73 extends the PVARP. The PVARP may be extended, for example, as previously described, by adding a PVARP extension to a base PVARP. The PVARP extension may also be a fixed value preset by the manufacturer or may be programmable.

The process 200 then advances to decision block 208. Here it is determined if the conditions exist to restore the AV interval back to the base AV interval. This may occur, for example, if there has been a ventricular pacing pulse issued in the demand mode with the extended AV interval. Different or additional criteria may be imposed on this step without departing from the invention. If the AV interval is to be restored to the base value at 208, the process advances to activity block 210 where the hysteresis circuit 71 restores the AV interval to the base value. Next, in activity block 212, the refractory circuit 73 restores the PVARP to the base PVARP value. The process then is done and returns to start.

If in decision block 208, restoration of the AV interval to the base value is not to occur, the process advances to decision block 214 to determine if a retrograde P wave has been sensed during the extended PVARP. If a retrograde P wave has not been sensed during the extended PVARP, the process returns to decision block 208. If a retrograde P wave has been sensed, the process advances to decision block 216 to determine if the extended AV interval has allowed an arrhythmic rhythm to occur over a series of N cardiac cycles, such as an RNRVAS rhythm or AVNRT rhythm. If not, the process advances to activity block 210. If, however, an arrhythmic rhythm has developed, such as an RNRVAS rhythm or AVNRT rhythm, the process advances to activity block 218 where the therapy control 75 causes the appropriate therapy to be administered by the device.

If, for example, the arrhythmic rhythm is an RNRVAS, the therapy control 75 may lengthen the atrial escape interval for at least one cycle as described in the aforementioned U.S. Pat. No. 6,498,949, incorporated in its entirety herein by reference. If the arrhythmic rhythm is an AVNRT, the extended PVARP may be shortened, e.g., restored to its base value, thus allowing the retrograde P wave to be detected and a ventricular pulse triggered at a shorter PV delay that starts with the P refractory event.

Following activity block 218, the process then advances to activity block 210 for restoration of the AV interval to the base interval and to activity block 212 for restoration of the PVARP to the base PVARP, if not already done during arrhythmic treatment. The process then is done and returns to start.

Figure 5:
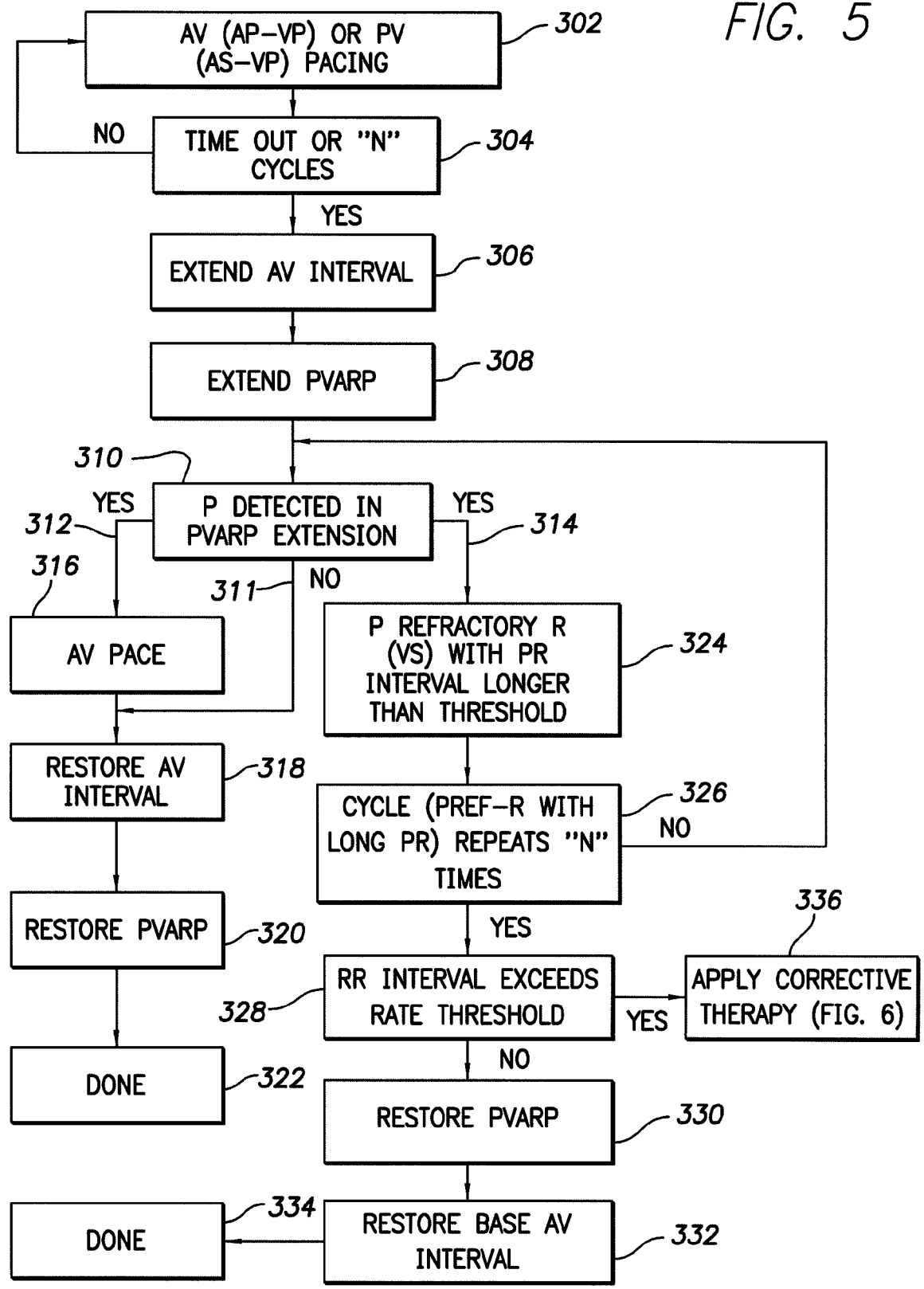
FIG. 5 illustrates a flow chart of a process carried out in connection with identification and management of a reentrant tachycardia in accordance with one embodiment of the present invention.

FIG. 5 illustrates a flow chart of a processing sequence carried out in connection with identification and management of reentrant tachycardia types of arrhythmia rhythms. Flow begins as block 302, where an atrial pacing pulse (AP) is delivered followed by a ventricular pacing pulse (VP). Alternatively, at block 302, an intrinsic P wave may be sensed (AS) followed by a ventricular pacing pulse (VP). At block 302, the ventricular pacing pulse follows the atrial pacing pulse or sensed P wave by the AV pacing delay. At block 304, it is determined whether a timer of the AV hysteresis circuit 71 has timed out or a programmed number of cycles have passed. When the decision as block 304 is YES, flow moves to block 306 where the AV hysteresis circuit 71 is activated and the AV interval is extended. At block 308, the refractory circuit 73 extends the PVARP interval.

At block 310, a determination is made as to whether an intrinsic P wave was sensed during the extended PVARP interval. When no intrinsic P wave is detected in the extended PVARP interval, flow moves along path 311 to block 318. When an intrinsic P wave is detected by the atrial sensing circuit 82 at block 310, flow moves along one of branches 312 and 314 depending upon whether the reentrant conduction detector 63 has been enabled. When the reentrant conduction detector 63 is disabled, flow moves to branch 312. At block 316, a ventricular pacing pulse is delivered following an AV pacing interval in accordance with a programmed AV pacing therapy. At block 318, the extended AV interval is restored to the base AV interval. At block 320, the extended PVARP interval is restored to the base PVARP interval. At block 322, flow returns to block 302.

The retrograde P wave may conduct to the ventricle, which may initiate an intrinsic R wave. If left uncorrected, the intrinsic R wave, resulting from the retrograde P wave, may reset the associated timers in the device 10. This may cause the device 10 to determine that no corrective therapy is needed. Embodiments of the present invention seek to recognize the intrinsic P wave as a retrograde P wave, and seek further to identify reentrant tachycardia, such as AVNRT, AVRT, and the like.

Returning to the determination at block 310, when the reentrant conduction detector 63 is enabled and a P wave is detected in the extended PVARP internal, flow moves along branch 314. At block 324, it is determined whether an intrinsic R wave has been sensed by ventricular sensing circuit 84. When an intrinsic R wave is sensed, reentrant conduction detector 63 may analyze one or more of various timing parameters. By way of example only, the timing parameters may include one or more of the PR interval, the RP interval and the R to R interval.

The PR interval is the time delay between the retrograde P wave and the next intrinsic R wave. The RP interval is the time delay between the intrinsic R wave and the next retrograde P wave. The R to R interval is the time delay between two successive intrinsic R waves. The reentrant conduction detector 63 compares one or more of the timing parameters to corresponding thresholds (e.g., a PR threshold, a RP threshold and a rate threshold). The intrinsic R wave may follow the P wave by a relatively long period of time, in which case a long PR interval would exceed the PR threshold, or by a relatively short period of time, in which case a short PR interval would fall below the PR threshold. The PR interval may be of interest because, when a long PR interval occurs, the conductive pathways between the atrium and ventricle are permitted to recover from a refractory state. When the conductive pathways between the atrium and ventricle recover, they are again excitable. The RP interval may be of interest for similar reasons. The R to R interval may be of interest as it is used to calculate the heart rate.

In the example of FIG. 5, a programmable PR threshold may be set to distinguish between long and short PR intervals. At block 324, the PR interval is compared to the programmed PR threshold. In the example of FIG. 5, the PR interval exceeds the PR threshold. Thus, the possibility still exists that reentrant tachycardia could be occurring.

Before declaring the myocardium to be experiencing some type of intrinsic reentrant tachycardia, the patient should exhibit the arrhythmia for more than one cardiac cycle. The number of cardiac cycles may be programmable.

At block 326, the reentrant conduction detector 63 analyzes a predetermined number of N consecutive cardiac cycles to determine whether the conditions at blocks 310 and 324 have been satisfied. For example, it is determined whether a series of N cardiac cycles occurred in which an intrinsic P wave was detected in the extended PVARP interval, followed by an intrinsic R wave with a long PR interval exceeding the PR threshold. When the conditions at blocks 310 and 324 are satisfied for a sufficient number of N cardiac cycles, the reentrant conduction detector 63 determines that conditions still indicate that the patient may be experiencing an intrinsic reentrant tachycardia. Therefore, flow moves to block 328. At block 328, the R to R interval is compared to a rate threshold. If the R to R interval exceeds the rate threshold, flow moves to block 336 to initiate delivery of a therapy. If the R to R interval falls below the rate threshold, flow moves to block 330. The R to R interval is averaged over the N cardiac cycles to determine whether the average exceeds the rate threshold. If the conditions at blocks 310, 324, 326 and 328 are not satisfied for N cardiac cycles, the base PVARP interval is restored at block 330. Next, at block 332, the base AV interval is restored. Thereafter, flow returns at block 334 to block 302.

If the conditions at blocks 310, 324, 326 and 328 are satisfied for N cardiac cycles, the flow moves to block 336 where a corrective therapy is applied under control of the therapy control circuit 75. Exemplary therapies are discussed below.

Optionally, the analysis at block 324 of the PR interval may be omitted. Optionally, the analysis at block 328 of the R to R interval may be omitted. Optionally, the RP interval may be analyzed, relative to an RP threshold, in addition to or in substitution for one or both of the analyzes of the PR interval and R to R interval.

Figure 6:
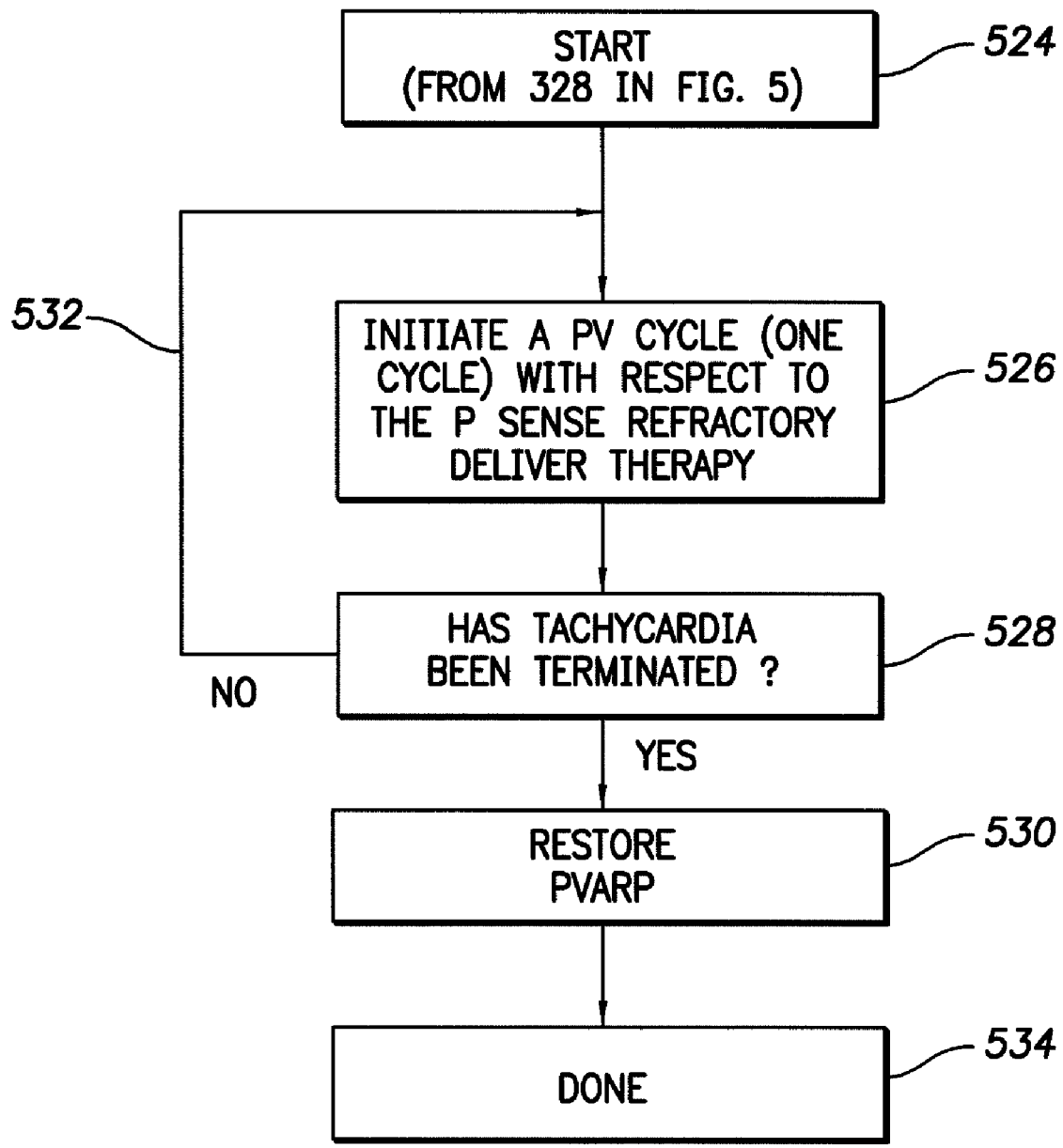
FIG. 6 illustrates a flow chart depicting a process carried out in connection with delivery of a control therapy in accordance with one embodiment of the present invention.

FIG. 6 illustrates a flow chart depicting a process carried out in connection with delivery of a control therapy when an intrinsic reentrant tachycardia is detected, such as through the process of FIG. 5. When flow enters block 524, it has already been determined that the intrinsic P wave has been refractory for a consecutive number of N cardiac cycles and the R to R interval corresponds to a heart rate above a programmable rate threshold. When the intrinsic P wave is identified to be refractory and the R to R interval for N cardiac cycles corresponds to an unacceptably high heart rate, flow moves to block 526.

At block 526, a corrective therapy is delivered. In the example of FIG. 6, the corrective therapy involves delivery of a stimulating ventricular pulse at a time following the intrinsic P wave in a subsequent cardiac cycle by an interval less than the AV pacing interval. The time at which of the corrective therapy is delivered may be based a measured or programmed interval. For example, the stimulating ventricular pulse may be delivered after a delay, following a retrograde P wave. The delay may be a percentage of the AV pacing interval, a percentage of the heart rate, a percentage of a measured PR interval and the like. For example, if the AV pacing interval is programmed to 180 msec, the ventricular pulse may be delivered with a delay set at 50% thereof, namely 90 msec after an intrinsic P wave is sensed. Alternatively, the delay of the corrective therapy may be a programmed fixed delay (e.g., 100 msec) or a programmed amount less than a measured or programmed interval (e.g., 50 msec less than the AV pacing interval, or 80 msec less than the PR interval, etc.).

The stimulus ventricular pulse may constitute a single pulse or series of pulses. The stimulus ventricular pulse may be provided at an amplitude similar to the amplitude of a pacing event or at a higher level. After delivery of the corrective therapy, flow moves to block 528 at which it is determined whether the reentrant tachycardia has been terminated. When the reentrant tachycardia has not been terminated, flow moves back along path 532 and an additional corrective therapy is applied at block 526. Optionally, the corrective therapy delivered at block 526 may be applied only a limited number of X times (e.g., 1-5 times). For example, at block 528, it may be determined that a corrective therapy has been applied five times, yet has not stopped the events believed to represent reentrant tachycardia. Once the programmed number of therapies is delivered, the corrective therapy is terminated and flow moves to block 530. At block 530, the base PVARP interval is restored and at block 534 flow returns to block 502.

Figure 7:
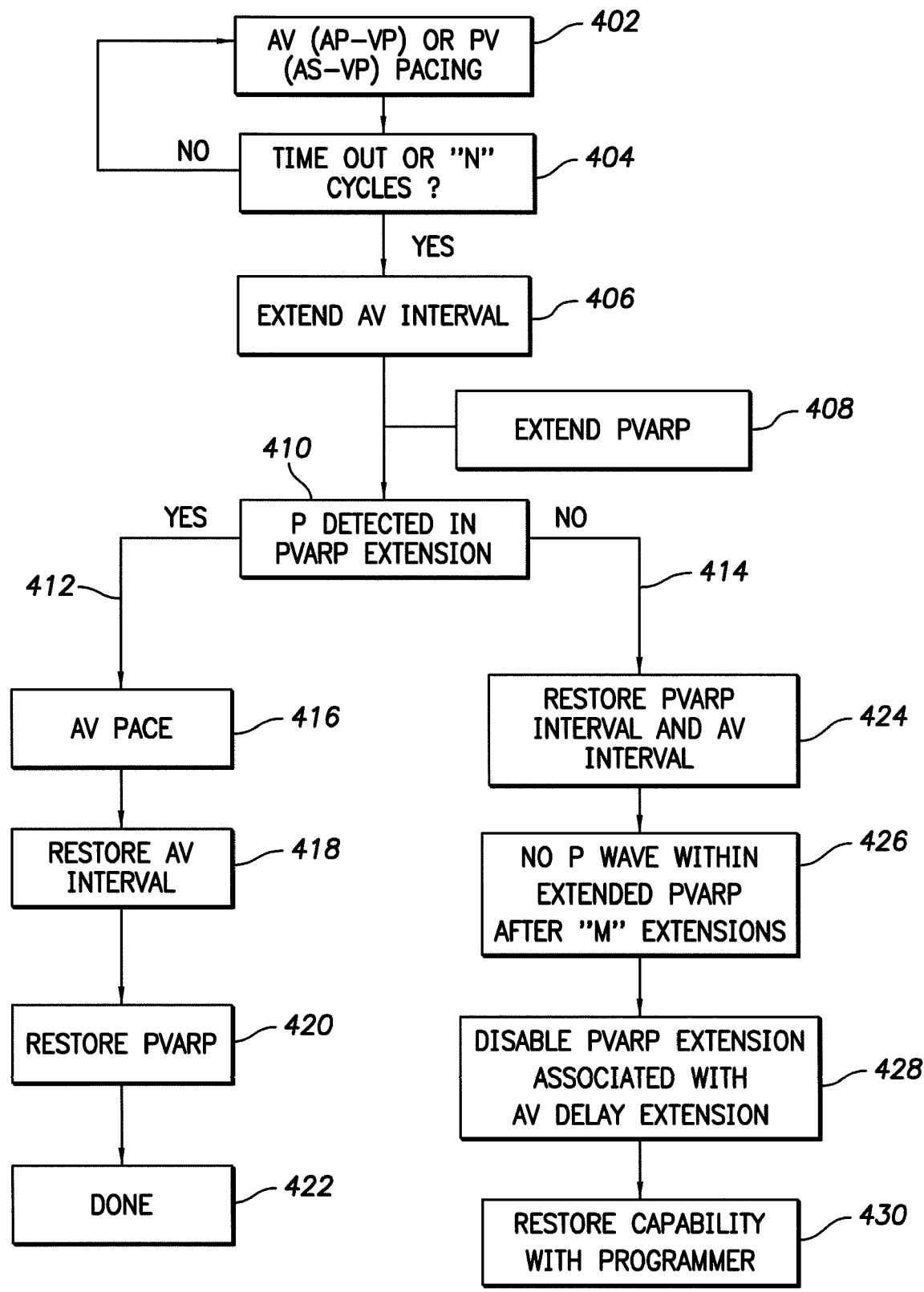
FIG. 7 illustrates a flow chart of the process carried out in accordance with one embodiment of the present invention.

FIG. 7 illustrates a flow chart of a processing sequence carried in connection with one embodiment. The embodiment of FIG. 7 represents one option for how the device 10 may be programmed to respond when no P waves are detected in the PVARP extension for a programmable number of M PVARP extensions. Flow begins at block 402, where an atrial pacing pulse AP is delivered followed by a ventricular pacing pulse VP. Alternatively, at block 402, an intrinsic P wave may be sensed followed by a ventricular pacing pulse. The flow through blocks 402-410 and 416-422 is similar to the flow at blocks 304-310 and 316-322 discussed above in connection with FIG. 5. For example, at block 404, it is determined whether an AV hysteresis timer has timed out or a programmed number of cycles have passed. At blocks 406 and 408, the base AV interval and base PVARP interval are extended. At block 410, it is determined whether an intrinsic P wave is detected within the extended PVARP interval. If yes, then flow moves through block 416 to block 422 where an AV pacing pulse is delivered and the AV and PVARP intervals are restored.

When no intrinsic P wave is detected in the extended PVARP interval at block 410, flow moves along path 414 to block 424. At block 424, the base PVARP and base AV intervals are restored. At block 426, the device 10 may be programmed to determine whether an intrinsic P wave has been detected for the extended PVARP interval in one or more of a programmable number of M extended PVARP intervals. When no intrinsic P wave is detected within the number of M extended PVARP intervals, the device 10 may optionally disable the PVARP extension functionality in connection with the AV hysteresis algorithm. Thus, at block 428, the PVARP extension functionality is disabled. At block 430, the PVARP extension functionality may be restored at any later time through an external programmer.

Figure 8:
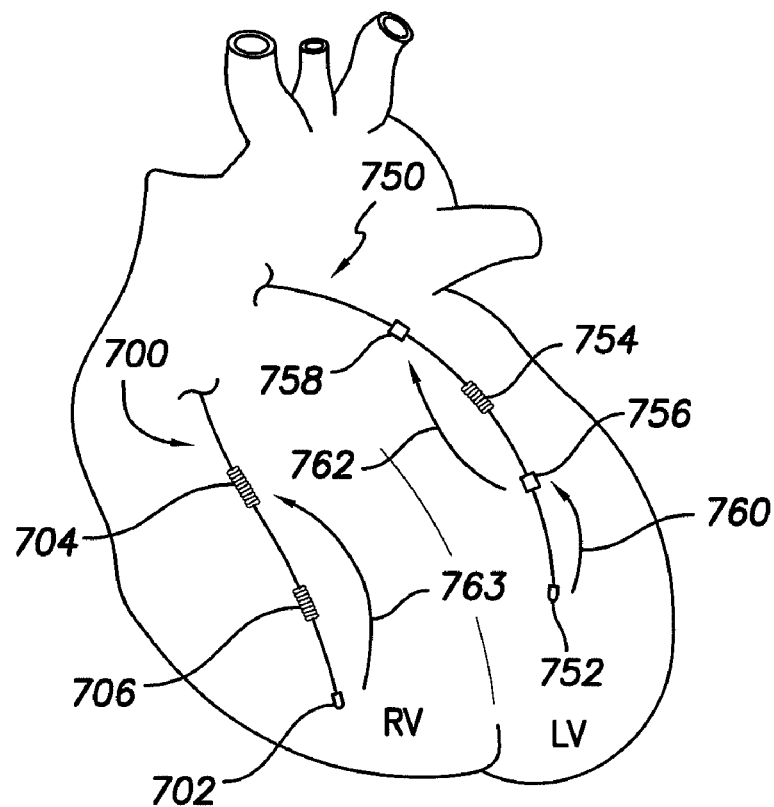
FIG. 8 illustrates an exemplary alternative configuration of electrodes that may be placed in or proximate the heart and used to deliver corrective therapy.

FIG. 8 illustrates an exemplary alternative configuration of electrodes that may be placed in or proximate the heart and used to deliver corrective therapy. In FIG. 8, a portion of a RV lead 700 and a portion of a LV lead 750 are illustrated. The RV lead 700 includes a RV tip electrode 702, a RV ring electrode 706, and a RV coil electrode 704. The LV lead 750 includes multiple electrodes, such as LV tip electrode 752, LV coil electrode 754 and LV intermediate electrodes 756 and 758. Optionally, additional or fewer electrodes may be provided on one or both of the RV and LV leads 700 and 750. The electrodes 702, 704, 706, and 752-758 may be used in various unipolar and bipolar combinations. For example, the therapy control module 75 may identify a bipolar configuration, in which a first vector 760 may be formed between the LV tip electrode 752 and LV ring electrode 754 to deliver a corrective therapy. Alternatively, the therapy control module 75 may identify a unipolar configuration, in which the LV tip electrode 754 is used alone. As a further option, one or more of electrodes 752-758 may be utilized in a unipolar configuration to deliver a first therapy and one more of electrodes 702-706 may be utilized in a unipolar configuration to deliver a second therapy. When a single electrode is inserted into the heart, the can or housing of the device may be used as another electrode when needed.

As a further example, combinations of electrodes 752-758 may be shorted together and used in unipolar or bipolar combinations. For example, electrodes 752 and 754 may be shorted together and assigned one polarity, whereas electrodes 756 and 758 are shorted together and assigned the opposite polarity to deliver an LV or RV therapy with a bipolar multi-electrode configuration. In the present example, the LV tip electrode 752 and intermediate electrode 754 form a first bipolar vector as noted by arrow 760, while electrodes 756 and 758 form a second bipolar vector as noted by arrow 762, both during a single therapy. Separately, electrodes 702 and 704 may be used to deliver the second therapy as a bipolar conduction vector 763.

Figure 9:
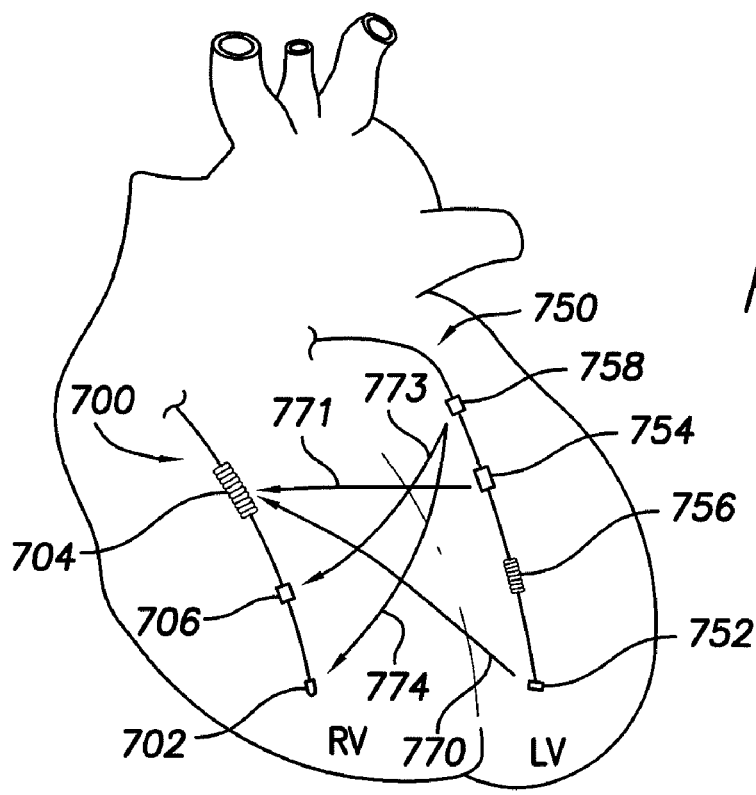
FIG. 9 illustrates an exemplary diagram of a heart, in which the lead is again located in the right ventricle and the lead is again located in the left ventricle.

FIG. 9 illustrates an exemplary diagram of a heart, in which the lead 700 is again located in the right ventricle and the lead 750 is again located in the left ventricle. In the example of FIG. 9, alternative conduction vectors are shown that may be provided in successive first and second therapies. For example, electrodes 752 and 754 may be shorted together and configured to form conduction vectors 770 and 771 with the RV coil electrode 704 in the right ventricle during a first therapy. During a second therapy, electrodes 758, 706 and 702 may be used to form conduction vectors 773 and 774.

As explained above, embodiments are presented that recognize the retrograde P wave followed by a native QRS complex associated with stable (repeating) RP and PR intervals that constitute reentrant tachycardia. In response thereto, a corrective therapy is delivered with an AV delay (PV or AS-VP) modified to usurp control from the native conductive pathways. Ventricular stimulus is delivered sufficiently early so that the ventricular paced complex encounters the retrograde pathway while physiologically refractory, thereby terminating the intrinsic reentrant tachycardia.

While the invention has been described by means of specific embodiments and applications thereof, it is understood that numerous modifications and variations may be made thereto by those skilled in the art without departing from the spirit and scope of the invention.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the timing dimensions, configurations and components described herein are intended to define parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112,sixth paragraph, unless and until such claim limitations expressly use the phrase "means for" followed by a statement of function void of further structure.

What is claimed is:

1. An implantable medical device, comprising:
a pulse generator configured to provide atrial and ventricular pacing pulses on demand, the pulse generator timing delivery of the ventricular pacing pulses based on an AV pacing interval;
an AV hysteresis module that extends an AV interval from a base AV interval to an extended AV interval to promote intrinsic heart activity;
a refractory module that establishes a PVARP interval equal to a base PVARP interval following at least one of the ventricular pacing pulses, the refractory module lengthening the PVARP interval by adding a PVARP extension to the base PVARP interval to provide an extended PVARP interval; and
a reentrant conduction detector identifying an intrinsic reentrant tachycardia based, in part, on a retrograde P wave occurring during the PVARP extension of the extended PVARP interval.

2. The device of claim 1, wherein the reentrant conduction detector identifies the intrinsic reentrant tachycardia based on intrinsic R waves sensed over N consecutive cardiac cycles at an R to R interval above a rate threshold.

3. The device of claim 1, wherein the reentrant conduction detector identifies the intrinsic reentrant tachycardia based on an intrinsic QRS complex having at least one of PR and RP intervals that exceed corresponding PR and RP thresholds.

4. The device of claim 1, wherein the AV hysteresis module restores the AV interval to equal the base AV interval and the refractory module restores the PVARP interval to the base PVARP interval responsive to delivery of a corrective therapy.

5. The device of claim 1, further comprising a therapy control module that directs the pulse generator to provide a corrective therapy responsive to the reentrant conduction detector identifying the intrinsic reentrant tachycardia.

6. The device of claim 5, wherein the therapy control module is configured to deliver the at least one of the ventricular pacing pulses as the corrective therapy timed to follow the retrograde P wave by a delay less than the AV pacing interval.

7. The device of claim 5, wherein the therapy control module is configured to cause the pulse generator to deliver the at least one of the ventricular pacing pulses, during the extended AV interval in connection with the corrective therapy.

8. The device of claim 5, wherein the therapy control module is configured to cause the pulse generator to repeat the corrective therapy on at least two successive cardiac cycles.

9. The device of claim 5, wherein the therapy control module is configured to cause the pulse generator to repeat the corrective therapy during a programmable number N of consecutive cardiac cycles.

10. The device of claim 1, where the intrinsic reentrant tachycardia is one of AV nodal reentrant tachycardia (AVNRT) and AV reentrant tachycardia (AVRT).

11. A method for managing an arrhythmia, comprising:
providing atrial and ventricular pacing pulses on demand, the ventricular pacing pulses being delivered based on an AV pacing interval;
extending an AV interval from a base AV interval to an extended AV interval;
establishing a PVARP interval equal to a base PVARP interval following at least one of the ventricular pacing pulses;
lengthening the PVARP interval by adding a PVARP extension to the base PVARP interval to provide an extended PVARP interval; and
identifying an intrinsic reentrant tachycardia based on a retrograde P wave occurring during the PVARP extension of the extended PVARP interval.

12. The method of claim 11, wherein the identifying operation identifies the intrinsic reentrant tachycardia based on intrinsic R waves sensed over N consecutive cardiac cycles at an R to R interval above a rate threshold.

13. The method of claim 11, wherein the identifying operation identifies the intrinsic reentrant tachycardia based on an intrinsic QRS complex having at least one of PR and RP intervals that exceed corresponding PR and RP thresholds.

14. The method of claim 11, further comprising restoring the AV interval to equal the base AV interval and the PVARP interval to equal the base PVARP interval responsive to delivery of a corrective therapy.

15. The method of claim 11, further comprising determining that a PR interval exceeds a PR threshold for a number of N consecutive cardiac cycles and, in response thereto, restoring the PVARP interval to equal to the base PVARP interval.

16. The method of claim 11, further comprising providing a corrective therapy when the intrinsic reentrant tachycardia is identified.

17. The method of claim 16, wherein the providing of the corrective therapy comprises delivering the at least one of the ventricular pacing pulses timed to follow the retrograde P wave by a delay less than the AV pacing interval.

18. The method of claim 16, further comprising delivering the at least one of the ventricular pacing pulses, during the extended AV interval, in connection with the corrective therapy.

19. The method of claim 16, further comprising repeating the corrective therapy during at least two successive cardiac cycles.

20. The method of claim 16, further comprising repeating the corrective therapy during a programmable number of N consecutive cardiac cycles.

21. The method of claim 11, where the intrinsic reentrant tachycardia event is one of AV nodal reentrant tachycardia (AVNRT) and AV reentrant tachycardia (AVRT).

* * * * *